United States Patent [19]
Nachlas et al.

[11] Patent Number: 5,338,623
[45] Date of Patent: Aug. 16, 1994

[54] SERIES TUBULAR DESIGN FOR SOLID ELECTROLYTE OXYGEN PUMP

[75] Inventors: Jesse A. Nachlas; Dale M. Taylor, both of Salt Lake City; Merrill A. Wilson, West Jordan, all of Utah

[73] Assignee: Ceramatec, Inc., Salt Lake City, Utah

[21] Appl. No.: 843,303

[22] Filed: Feb. 28, 1992

[51] Int. Cl.⁵ .............................................. H01M 8/12
[52] U.S. Cl. ......................................... 429/31; 429/35
[58] Field of Search ......................... 429/30, 31, 33, 35

[56] References Cited

U.S. PATENT DOCUMENTS

| | | |
|---|---|---|
| 3,402,230 | 9/1968 | White .................................. 429/31 |
| 4,197,362 | 4/1980 | Schmidberger et al. . |
| 4,385,101 | 5/1983 | Catanzarite . |
| 4,431,715 | 2/1984 | Isenberg . |
| 4,648,945 | 3/1987 | Isenberg . |
| 4,725,346 | 2/1988 | Joshi . |
| 4,728,584 | 3/1988 | Isenberg ............................. 429/31 |
| 4,786,395 | 11/1988 | Otsuka et al. . |
| 4,791,035 | 12/1988 | Reichner ............................ 429/31 |
| 4,879,016 | 11/1989 | Joshi . |
| 5,021,137 | 6/1991 | Joshi et al. . |
| 5,034,288 | 7/1991 | Bossel . |
| 5,045,169 | 9/1991 | Feduska et al. . |
| 5,063,122 | 11/1991 | Rohr . |
| 5,064,734 | 11/1991 | Nazmy . |

OTHER PUBLICATIONS

Figure 5-1a, Figure 5-1b, "Fuel Cells", DOE/MET-C-86/0241, Technology Status Report, Morgantown Energy Technology Center, Morgantown, W. Va., (1986).

Primary Examiner—Stephen Kalafut
Attorney, Agent, or Firm—Trask, Britt & Rossa

[57] ABSTRACT

An electrochemical device is disclosed comprising a plurality of electrolytic cells, each having an oxygen ion-conducting electrolyte, an anode and a cathode associated with the electrolyte, conductive interconnecting structures electrically connecting the anode of each electrolytic cell to the cathode of an adjacent tubular cell, and sealing means positioned between the interconnecting structure and the electrolytic cells to provide a gas-tight seal therebetween. The configuration of the interconnecting structure and the placement of the seal means provides a separation between the seal and the conductive pathway of electrons between the anode and cathode to prevent corrosion or deterioration of the seal thereby compromising the pneumatic integrity of the device. Also disclosed are interconnecting and coupling structures providing the ability to manifold series of tubular electrolytic cells, the interconnecting and coupling structures being configured to maintain the electrical and pneumatic integrity of the device.

29 Claims, 5 Drawing Sheets

SERIES TUBULAR DESIGN FOR SOLID ELECTROLYTE OXYGEN PUMP

BACKGROUND

1. Field of the Invention

This invention relates to solid-state electrochemical devices capable of transporting ions through an electrolyte. Specifically, this invention relates to apparatus for the transport of ions through series tubular structures having improved electrical and pneumatic integrity.

2. Statement of the Art

Conductive solids which transport ions, such as oxygen ions, are known in the art and are useful in many applications, including fuel cells, gas production and separation/purification, and gas sensing or monitoring. In certain applications, a series of tubular electrolytic cells joined together provide increased electrochemical operation. An example of a series tubular system used as a fuel cell is disclosed in U.S. Pat. No. 4,431,715 to Isenberg, issued Feb. 14, 1984.

Efficient operation of series tubular cells has been compromised in prior art systems by inherent weaknesses in system design and configuration. For example, individual electrolytic cells are joined together by means generally known as an interconnect, which seals the tubes together and provides an electrical connection therebetween. However, prior art interconnects often fail because of degradation of the seal. The high temperatures at which electrolytic cells operate cause corrosion between the electrical conductor and the seal of the interconnect and sealing integrity is lost.

In addition, it has been difficult to produce an effective seal for use with high efficiency electrolytes or electrodes because of high operating temperature conditions. That is, when using silver or silver alloy based electrodes, for example, the maximum temperature of the sealing material is limited to the melting point of silver or silver alloy. Yet, the glass must maintain sufficient viscosity at such high operation temperatures to retain a seal over sustained periods of time.

Further problems have been experienced in prior art series tubular cells due to limitations experienced in configuring multiple cells in an efficient manner. With prior art systems, the interconnects limit the amount of manifolding which can be done with the tubes. The prior art interconnects currently used do not allow variation in configuration and manifolding because of a loss in pneumatic integrity of such systems.

Thus, it would be an improvement in the art to provide a series tubular electrochemical system having improved interconnects between the tubes to assure electrical and pneumatic integrity of the system and to provide sealing integrity between the tubes. It would be a further improvement in the art to provide a series tubular electrolytic cell system which provides simple interconnection of the tubes while permitting variation in manifolding and configuration.

SUMMARY OF THE INVENTION

In accordance with the present invention, solid-state electrochemical structure for transporting ions includes a plurality of tubular electrolytic cells joined together in series with electrical conductor means configured to provide electrical interconnection between each tubular electrolytic cell, and further including sealing means for securing each electrical conductor to the tubular cells with which each is associated to provide a pneumatic seal.

The tubular cells of the structure are generally cylindrical bodies having a thin wall with external and internal opposing surfaces. The tubular cells are adapted to receive gases therein, and each tubular cell is open at both ends thereby providing communication between the cells when the tubular cells are placed end-to-end. The wall of the cylinder serves as the electrolyte, and may preferably be made of ceramic metal oxides such as zirconia, ceria, hafnia, bismuth oxide or the like when oxygen ion transport is desired. Electrolytes of this type are disclosed in U.S. Pat. Nos. 4,725,346; 4,879,016; and 5,021,137, the contents of each being incorporated herein by reference. The ceramic used in the electrolytes may be doped with other materials, such as calcia. Electrolytes such as betaalumina, NASICON and the like may be used if sodium ion transport is desired.

The electrolyte, or wall of the tubular cell, is preferably thin, having a thickness of from about 1 millimeter to about 25 millimeters. A preferred thickness is from about 5 mm to about 10 mm. The electrolyte is non-porous in order to prevent escape of gas from within the tubular cell.

An anode is associated with one surface of the tube, either the interior surface or the exterior surface, while a cathode is associated with the opposing surface. In a particularly suitable tubular cell, the anode is in the form of a coating adhered to the inner surface of the tube and the cathode is in the form of a coating adhered to the outer surface. Each tubular cell of a multi-cell structure has the anode thereof associated with the same surface as every other tubular cell.

The anode and cathode are porous or permeable to gas molecules thereby allowing gas to penetrate the electrode. Materials which are particularly suitable for use as electrodes (i.e. the cathode and anode) in the instant structure are silver, alloys of silver and composites of silver and oxide ion-conductive materials. Such alloys and composites preferably contain a very high portion of silver (e.g. at least 50% silver). Metals which may be alloyed with silver or used instead of silver include palladium, platinum, gold and copper. In addition, some conductive ceramic oxides may be used in composites with silver, including lanthanum strontium manganite. The aforementioned materials are known to be particularly effective as electrodes for oxygen generation systems.

The anodic and cathodic materials may be applied to the respective surfaces of the tubular cell by means known in the art. Such application methods include sintering of a paste material, plasma spraying or sputtering. The coating of electrode material on the electrolyte is substantially continuous, i.e. there are no spaces or breaks in the coating. The placement of the anode on one surface of the electrolyte is preferably co-extensive with placement of the cathode on the opposing surface. The thickness of the anode or cathode on the ceramic electrolyte is generally between about 10 microns and about 30 microns, and preferably between about 15 to about 20 microns. The electrode layers are preferably thin in order to allow movement of gases freely therethrough. When very thin electrodes are used it may be desirable to use a current conductor, such as a metallic grid, over the electrode to maintain the sheet resistance. From an ion transport standpoint, very thin electrolytes are also preferred so long as molecular gas integrity is maintained. From a structural standpoint, thicker electrolytes may be required, especially if there is, or could be, a significant pressure differential across the electrolyte.

The tubular cells of the structure are connected end-to-end in series by electrical conductors, or interconnects. Aligning the individual tubular cells is more advantageous than a single long tubular cell because the electrons have a shorter distance to travel and sheet resistance is reduced accordingly. Further, a lower current is required for an equivalent amount of oxygen production. The interconnects are configured to form an electrical connection between the anode of one cell and the cathode of the adjacent cell. The interconnects are formed of highly conductive material which is preferably resistant to oxidation. The material used for the interconnects must also have a thermal expansion rate comparable to that of the material used to form the tubular cells. Thus, when the tubular cells expand under high temperature, the interconnects will similarly expand without damage to the individual cells or interconnects.

Examples of materials which may be used to form the interconnects include semiconducting oxides like LSM (lanthanum strontium manganite), LSCr (lanthanum strontium chromite), LCM (lanthanum calcium manganite) and similar materials, and high chrome metal alloys such as Inconel® (600 series) (76% Ni, 15.5% Cr, 8% Fe) or stainless steel (400 series) and similar corrosion resistant metals. A particularly suitable material for the interconnect is $La_{.5}Sr_{.5}MnO_3$.

The interconnects are Joined to the tubular cells by sealing means which provide a gas-tight seal thereby preventing leakage of oxygen or other gases from within the tubular cells. Sealing means are formed between the electrolyte and the interconnect in a manner which provides a separation between the electrical pathway and the sealing means. Separation of the sealing means from the electrical pathway, in addition to the configuration of the interconnect, prevents deterioration of the seal resulting from high temperature operation of the electrochemical device.

The sealing means comprises a sealant material which provides a comprehensive, gas-tight barrier between the interconnect and the tubular cell at high operating temperatures, typically about 600° C. to about 800° C. The sealant material must also have a thermal expansion rate comparable to that of the interconnect material and the electrolyte. A particularly suitable sealant is a devitrifying glass, i.e. a glass material which, after being melted and thermally treated, converts to a glass-/ceramic upon cooling. An exemplar such material is a lithium alumino-silicate.

In a first embodiment, an interconnect having a bell-shape is positioned between two tubular cells and communicating layers of conductive material join the anode of one cell to the interconnect, and join the interconnect to the cathode of an adjacent cell to form an electron path between the electrodes via the interconnect. Sealant is placed relative to the interconnect and the tubular cells in a manner which forms a seal therebetween but is remote from the electrical pathway of the interconnect. The conductive material positioned between the electrode and the interconnect may be conductive metals such as silver, silver alloys, platinum and the like.

In an alternative embodiment, a collar of material is positioned around both ends of each tubular cell, and the interconnect is positioned between the collars of adjacent cells. Particularly suitable materials for the collars are oxidation-resistant ceramics, such as ceria or calcia doped ceria, which have a thermal expansion comparable to the electrolyte with which the collars are associated. The material used for the collars may also be ion-conducting. Other suitable materials include any inert material which has a thermal expansion comparable to that of the electrolyte, such as stainless steel or forsterite (a composite magnesium silicate oxide).

The collars may be secured to the ends of the tubular cells by co-sintering or by application of a high temperature material such as aluminosilicate glass. Sealant is then positioned between the collars and the interconnect to effect a gas-tight seal. This embodiment provides a configuration with less restrictive tolerances in registration between the tubular cells and the interconnect, and creates a stronger, more reliable seal.

The geometrical configuration of the interconnects permits manifolding, or stacking, of numerous tubular cells while maintaining electrical and pneumatic integrity of the system. End caps and coupling structure are provided which, when placed at the end of a series of tubular cells, permits stacking, or aggregation, of numerous tubular cells. There is provided a positive end cap which forms an electrical connection with the anode of a terminal tubular cell, and a negative end cap which forms an electrical connection between the cathode of a terminal tubular cell. The end caps are made from conductive materials as described previously in connection with the interconnects. The end caps are formed to the ends of the tubular cells as described with respect to the interconnects, and sealing means are positioned to provide a pneumatic seal.

Coupling structures are secured between the negative end cap of one series of tubular cells and the positive end cap of another series of tubular cells. The coupling structure forms an electrical connection between the separate series of electrolytic cells, and communicates gases between adjacent series of cells. The coupling structure is formed to the end caps in a manner which provides a gas-tight seal.

BRIEF DESCRIPTION OF THE DRAWINGS

In the drawings, which illustrate what is currently considered to be the best mode for carrying out the invention.

DETAILED DESCRIPTION OF THE ILLUSTRATED EMBODIMENTS

Figure 1:
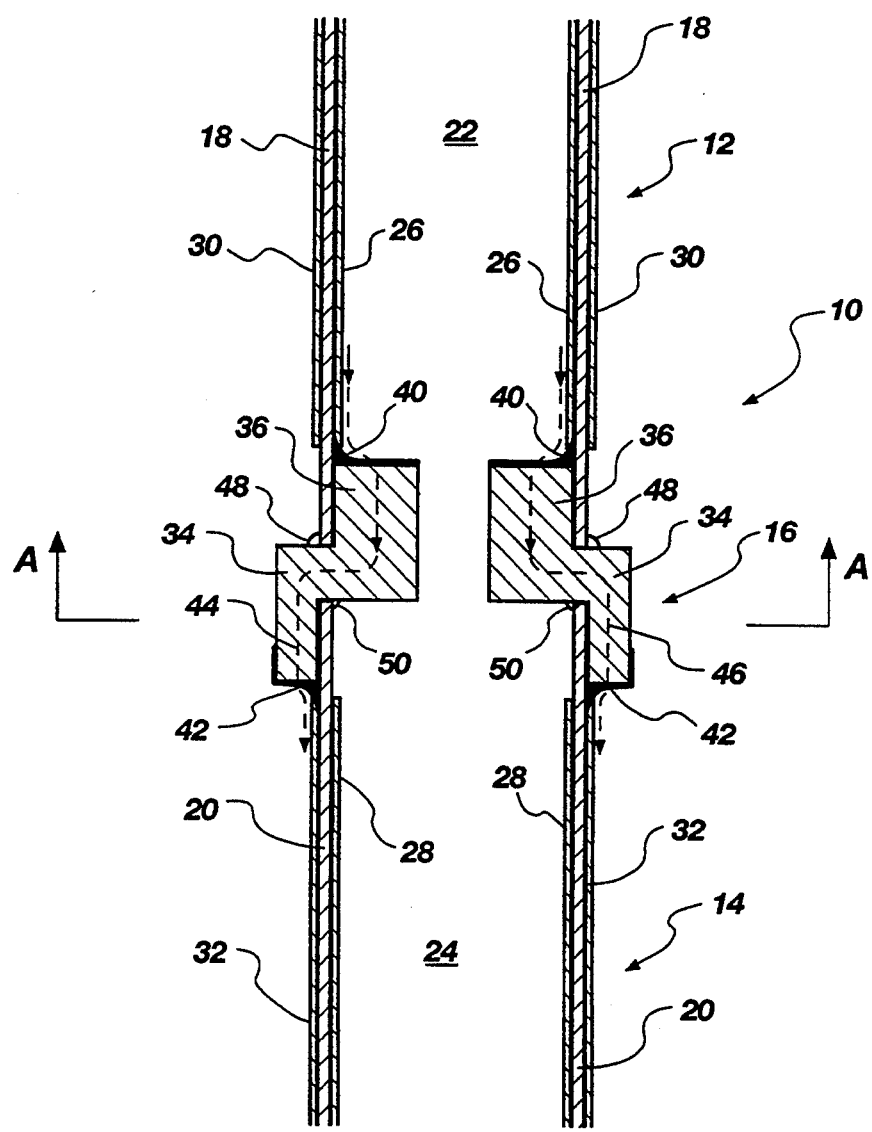
FIG. 1 is a view in longitudinal cross section illustrating the interconnect positioned between a first tubular cell and a second tubular cell.

As shown by FIG. 1, the electrochemical structure 10 of the invention includes a plurality of electrolytic cells 12, 14 joined together by a bell-shaped interconnect 16. The electrolytic cells 12, 14 are cylindrical tubes having a wall 18, 20 which forms the electrolyte. The wall 18, 20 forms an internal space 22, 24 within which gases are formed during operation of the electrochemical structure 10. A suitable material for forming the cell 12, 14, and thus the electrolyte 18, 20, is ceria. The wall 18, 20 of the electrolytic cell 12, 14 is about 5 mm thick.

An anode 26, 28 is formed to the interior surface of the concentric wall 18, 20 of the cells 12, 14. The anode 26, 28 is a coating of LSCo (lanthanum strontium cobaltite) with an intermediate coating of LSCo and silver applied to the wall 18, 20, The coating can be attached by sintering of a paste or by sputtering, a technique well known in the art. The thickness of the LSCo-silver anode 25, 28 is about 20 microns.

A cathode 30, 32 is formed to the exterior surface of the concentric wall 18, 20 of the cells 12, 14. The cathode 30, 32 is a coating of LSCo placed on the electrolyte with an intermediate coating thereover of LSCo-silver alloy having at least 50% silver as a component thereof. The cathode 30, 32 is formed to the wall 18, 20 in a manner similar to that of the anode 26, 28. The thickness of the cathode material is about 20 microns. The coating of the anode 26, 28 on the interior surface of the wall 18, 20 is coextensive with the coating of the cathode 30, 32 on the exterior surface of the wall.

Figure 2:
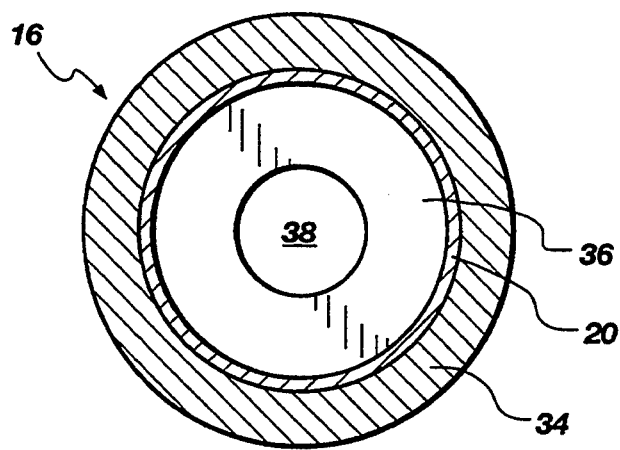
FIG. 2 is a view in cross section of the interconnect taken at line A—A in FIG. 1.

Adjacent tubular electrolytic cells 12, 14 are joined together by an interconnect 16. As illustrated in FIG. 2, the bell-shaped interconnect 16 is circular having an outer cap 34 and an inner sleeve 36. The outer cap 34 is sized to surround and receive the end of one tubular cell 14 and to come into registration with the exterior surface of the wall 20 of that tubular cell 14. The inner sleeve 36 is sized to fit within and register against the interior surface of the wall 18 of an adjacent tubular cell 12. A central void 38 provides communication between the interior 22 of one tubular cell 12 and the interior 24 of the adjacent tubular cell 14.

As illustrated by FIG. 1, the inner sleeve 36 of the interconnect 16 is adjacent the anode 26 of tubular cell 12. A conductive material 40, such as silver or silver alloy, is formed between the anode 26 and the interconnect 16. Similarly, the outer cap 34 of the interconnect 16 is adjacent the cathode 32 of tubular cell 14, and a conductive material 42 is formed between the interconnect 16 and the cathode 32. The conductive material 40, 42 serves to direct electrons from the anode 26 to the interconnect 16, and from the interconnect 16 to the cathode 32. The pathway which the electrons travel is indicated by the broken arrows 44, 46.

To effect a pneumatic seal between the tubular cells 12, 14 and the interconnect 16, sealing means in the form of a sealant are positioned therebetween. That is, a sealant 48 of devitrifying glass is formed about the interconnect 16, where the end of the tubular cell 12 meets the outer cap 34, by placement of a bead of glass material thereabout. The bead is then heated to melt the material. The devitrifying glass material has a melting point less than that of the silver or silver alloy electrodes, and heating of the sealant to form the seal does not affect the electrode material. Upon cooling, the devitrifying glass turns to a glass/ceramic. A similar bead of devitrifying glass sealant 50 is positioned between the interior surface of the adjacent tubular cell 14 and the interconnect 16, and is heated and cooled to form a gas-tight seal.

It is notable that the sealant 48 on the exterior of the interconnect 16 is positioned so that it is separated from the electron pathway of the interconnect 16. Likewise, the sealant 50 on the interior of the interconnect 16 is separated from the electron pathway of interconnect 16. By the positioning of the sealing means, the seals are spaced apart from the interconnect and also preferably from the electrodes in a manner which prevents corrosion of the sealing means when the electrochemical cell is operating at high temperatures.

The electrochemical cell is produced by first applying a coating of LSCo to both the interior and exterior surfaces of the tube. The tubes are then fired to about 1120° C. An intermediate coating of a mixture of LSCo and silver palladium alloy is then placed on the LSCo coatings of the interior and exterior surfaces of each tube. A particularly suitable composition for the intermediate coating is about 75% LSCo to about 25% silver-palladium alloy. The ratio of silver to palladium in the alloy may vary, but a ratio of 70% to 30% is suitable. The intermediate coating is fired to both surfaces of the tubes at about 1120° C. A coating of silver is then placed on the interior surface of each tube to form current collector means on the anode 26, 28 of each tube. The silver coating is fired at about 750° C.

The tubes are then joined end-to-end by attachment of the interconnects. The interconnects are formed to tubes by application of the devitrifying glass, and the tubes are fired at about 940° C. A silver coating is then placed on the exterior surface of each tube to provide a current collector means on each cathode. The interconnected tubes are fired again at 750° C. The formation of the silver coating on the cathode, following application and firing of the devitrifying glass, is particularly important to operation of the electrochemical cell since firing of the silver coating on the cathode at high temperatures, if applied before the application and firing of the devitrifying glass, would degrade the performance of the current collector.

Figure 3:
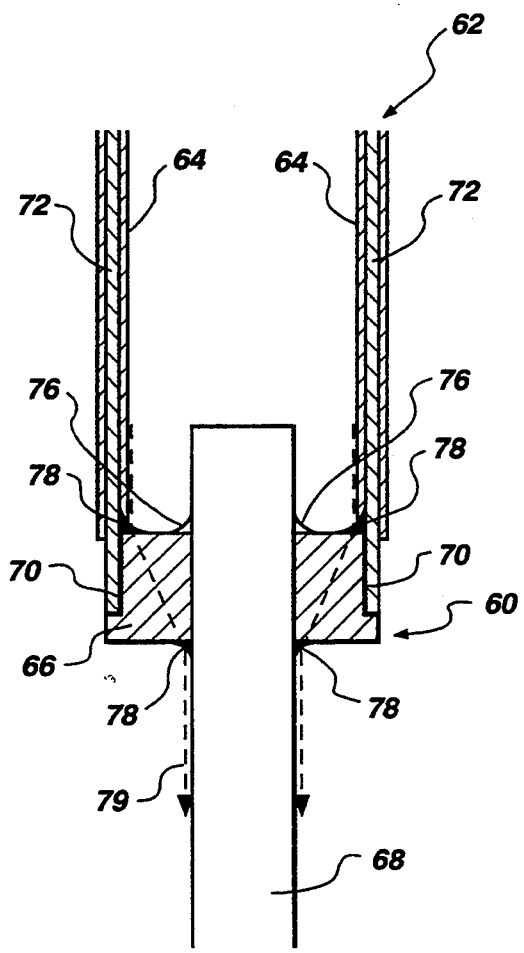
FIG. 3 is a view in longitudinal cross section of a positive end cap of the invention.
Figure 4:
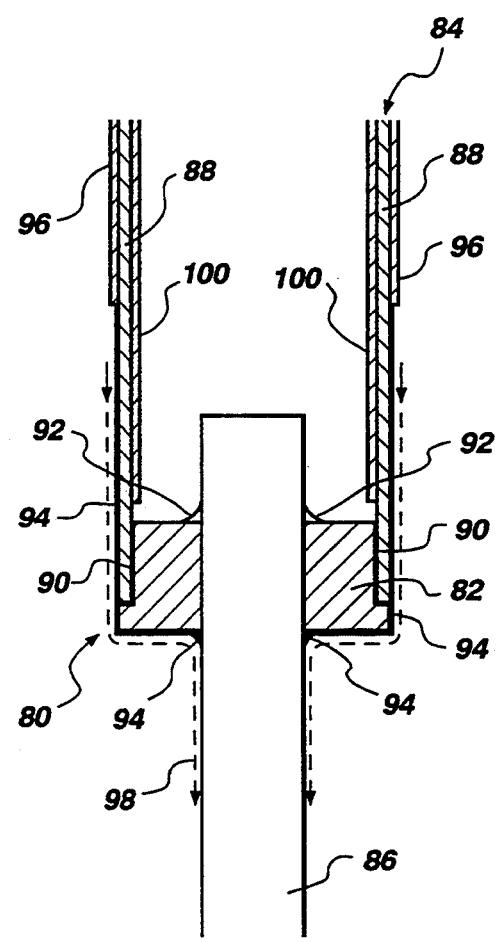
FIG. 4 is a view in longitudinal cross section of a negative end cap of the invention.
Figure 5:
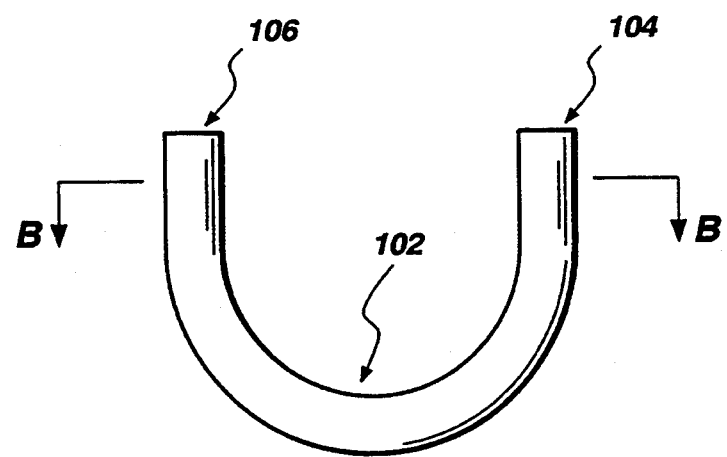
FIG. 5 is a plan view of a coupling structure.

In operation, an electrical current is applied to the electrodes at the beginning tubular cell of the series. Electrons flow from the anode on the inner surface of a tubular cell, through the pathway of the interconnect, and to the cathode of the adjacent tubular cell. When the series tubular system is used, for example, in the production of oxygen gas, air or other oxygen-containing gas surrounds the outside of the tubular cells. Electrons at the cathode ionize oxygen atoms to oxygen ions. The oxygen ions pass through the electrolyte via the influence of a voltage differential into the interior of the tubular cell where the electrons are given up to the anode and oxygen atoms are formed inside the tubular cells. The electrons given up at the anode continue to travel through the interconnect and to the cathode of an adjacent cell where the process continues at that cell. The reaction to form oxygen atoms can be expressed as cathode $O_2 + 4\ e \rightarrow 2O+$ anode $2O-- \rightarrow O_2 + 4\ e$ A plurality of tubular cells joined in series can be further joined to another plurality of tubular cells joined in series to provide an integrated system of interconnected electrolytic cells. End caps and coupling structure, as illustrated in FIGS. 3, 4 and 5, are used to join separate series of tubular cells together. A positive end cap 60, as shown by FIG. 3, is attached to one end of a tubular cell 62 to direct electrons from the anode 64. The positive end cap 60 comprises a cap 66 which inserts into the end of the tubular cell 62. The cap 66 is formed of the same materials as previously described in connection with the interconnect, namely a highly conductive, oxidation-resistant material having a thermal expansion comparable to that of the tubular cell material. A particularly suitable material is LSM (La$_{.5}$Sr$_{.5}$MnO$_3$). Through the positive end cap 66 is positioned a hollow conduit 68 of stainless steel 446.

The end cap 60 is joined to the tubular cell 62 by sealing means to pneumatically seal the system. Sealant 70, such as a devitrifying glass, is positioned between the electrolyte 72 and the cap 66. The sealant 70 is heated and then cooled as described previously in connection with sealing of the interconnect. A bead of sealant 76 is also positioned between the hollow conduit 68 and the cap 66, interior to the tubular cell 62. The sealant 76 is melted and then cooled to form a gas-tight seal around the hollow conduit 68. The sealant 70, 76 is positioned to be separated from the conductive pathway of electrons traveling through the cap 66.

A bridge of electrically conductive material 78 is formed between the anode 64 and the cap 66 on the interior surface of the tubular cell 62. Electrically conductive material 78 is also formed between the cap 66 and the hollow conduit 68 on the exterior surface of the end cap 60. The electrically conductive material is that as described above in connection with the interconnect, namely silver, silver alloys, platinum and the like. The conductive material 78 directs electrons from the anode through the cap 66 and to the hollow conduit 68, as indicated by the broken line 79. The hollow conduit 68 is also completely coated on the outer surface with silver. Although conductive ceramic oxides could be used as conductive material 78, metals are usually preferred because they are more malleable, especially at elevated temperatures.

The negative end cap 80, as shown in FIG. 4, also comprises a cap 82 which inserts into the end of a tubular cell 84 and a hollow conduit 86 positioned through the cap 82. As with the positive end cap 60 and the interconnects, the cap 82 is formed of a highly conductive, oxidation-resistant material which has a thermal expansion rate comparable to that of the tubular cell material. A particularly suitable material is LSM (La$_{.5}$Sr$_{.5}$MnO$_3$). The hollow conduit 86 is made from a conductive material, preferably stainless steel 446.

The cap 82 is sealed to the electrolyte 88 of the cell 84 by placement of a sealant 90 therebetween. A bead of sealant 92 is also positioned between the cap 82 and the hollow conduit 86. The sealants 90, 92 are preferably devitrifying glass as described previously. The sealant is heated and then cooled to form a gas-tight seal between the end cap 80 and the tubular cell 84. The sealants 90, 92 are positioned to be separated from the conductive pathway of electrons.

Conductive material 94, suitably silver, silver alloys, platinum and the like, is applied to the outside of the tubular cell 84 and extends from the cathode 96, over the end cap 82, to the hollow conduit 86 and over the conduit 86. The conductive material 94 thus provides an electrical pathway for electrons to travel between the cathode 96 and the hollow conduit 86, as indicated by the broken line 98. It should be noted that the anode 100 of the tubular cell 84 does not contact the cap 82, as illustrated in FIG. 4, to avoid short circuiting of the cell.

Figure 6:
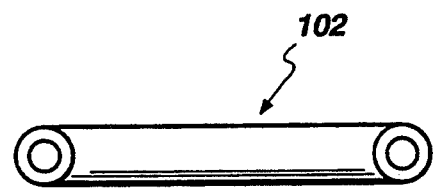
FIG. 6 is a view in cross section of the coupling structure shown in FIG. 5, taken at line B—B thereof.

Separate series of interconnected tubular cells may be formed together with a coupling structure 102, as shown in FIGS. 5 and 6. The coupling structure 102 may take any expedient shape or configuration, but is illustrated as a U-tube. One end 104 of the coupling structure 102 is connected to the positive end cap secured to the terminal cell of a first series of cells, and the other end 106 of the coupling structure 102 is connected to the negative end cap secured to a terminal cell of a second series of cells. The coupling structure is formed of a highly conductive, oxidation-resistant material. Suitable materials include Inconel ® and stainless steel. A particularly suitable material is stainless steel 316L.

The coupling structure 102 may be joined to the end caps by any suitable means, including welding, brazing, soldering, or the like. A particularly suitable means of joining the structures is silver brazing using a silver alloy brazing material containing copper, zinc, cadmium or similar material. A particularly suitable brazing material contains 45% silver, 30% copper and 25% zinc. Such alloys maintain efficient electrical conductivity in the area of the seal while providing a pneumatic seal. As shown by FIG. 6, the coupling structure 102 is hollow to provide communication of gases between a first series of tubular cells and a second series of cells. After brazing, the entire U-tube is coated with silver or silver alloy.

Figures 7, 8:
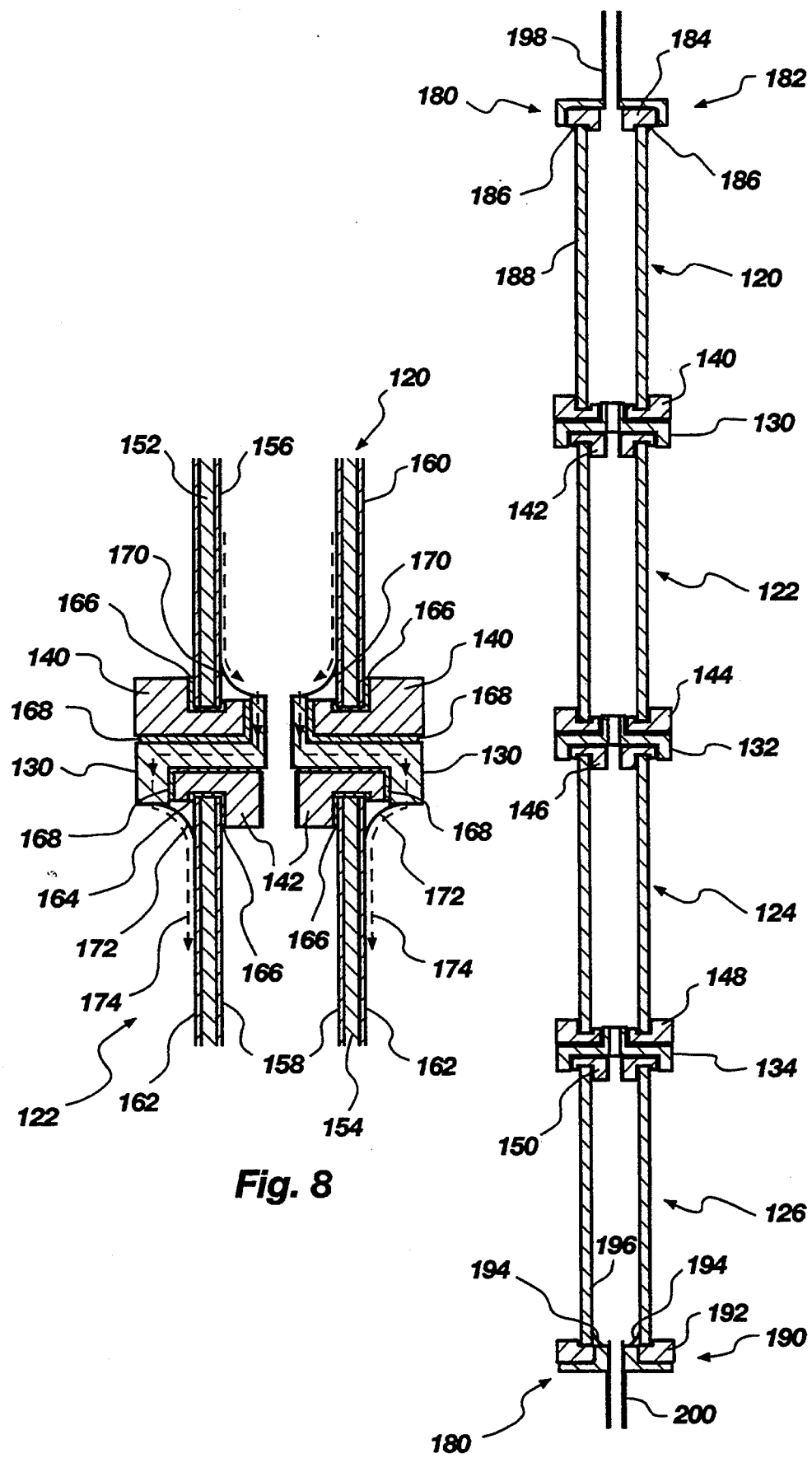
FIG. 7 is a view in longitudinal cross section of a series of interconnected cells illustrating an alternative embodiment of the invention.
FIG. 8 is an enlarged view of the interconnect illustrated in FIG. 7.

In an alternative embodiment, as illustrated by FIGS. 7 and 8, tubular electrolytic cells 120, 122, 124, 126 are joined together by interconnects 130, 132, 134 as previously described, except that collars 140, 142, 144, 146, 148, 150 are associated with the ends of each tubular cell 120, 122, 124, 126 which interface with the interconnects 130, 132, 134. Collars 140, 142, 144, 146, 148, 150 associated with the ends of the tubes provide greater sizing tolerances between the tubular cells and the interconnects, and simplify sealing the cells to the interconnects. The integrity of the seal is also increased as a result of increased sealing area.

As more clearly illustrated in FIG. 8, a first electrolytic cell 120 is joined to a second electrolytic cell 122 with an interconnect 130. The electrolytic cells 120, 122 are cylindrical, and the wall forms the electrolyte 152, 154 of the cells 120, 122. An anode 156, 158 is formed to the inner surface of the electrolyte 152, 154, and a cathode 160, 162 is formed to the exterior surface of the electrolyte 152, 154 by application of a coating of LSCo and an intermediate coating of LSCo-silver alloy, as previously described. A silver coating is then applied to the interior surface of each cell at previously described.

Collars 140, 142 are associated with the ends of the electrolytic cells 120, 122. The collars 140, 142 are typically made of the same ceramic material of which the electrolyte is made. The collars thus have a comparable thermal expansion rate as the electrolyte. The collars are constructed of an oxidation-resistant material such as zirconia, hafnia, bismuth oxide, ceria or similar materials. Ceria is particularly suitable. Ceria and other ceramics may also be doped with various materials, such as calcia. The material of the collars 140, 142 may or may not be the same as that from which the electrolytic cell is produced. It is important that the material of the collar has a thermal expansion rate comparable to that of the electrolytic cell material. The collars 140, 142 are annular disks having a groove 164 formed therein sized to receive the end of a cell. There need not be a close fit between the groove 164 and the end of the cell 122.

As illustrated, the collar 140, 142 may be secured to the end of the cell 120, 122 by placing a sealant 166 therebetween. The sealant 166 is a material which will maintain the seal under high temperature operating conditions. A particularly suitable material is a high-temperature glass such as aluminosilicate glass. Alternatively, the collars 140, 142 may be sintered to the ends of the cells 120, 122 by techniques known in the art. The collars 140, 142 are then sealed to the interconnect 130 by means of a sealant 168 such as devitrifying glass.

A silver coating which acts as a current collector is applied to the exterior surface of each tube, on the cathode, and is fired at 750° C., as previously described. Conductive material 170 is applied between the anode 156 of one electrolytic cell 120, the collar 140 and the interconnect 130 to effect a conductive pathway for electrons therebetween. Conductive material 172 is also applied between the interconnect 130, the collar 142, and the cathode 162 of the adjacent electrolytic cell 122 to complete the conductive pathway between the anode 156 and cathode 162 of adjacent cells. The pathway travelled by electrons is indicated by the broken line at 174. The conductive material 170, 172 is a highly conductive material such as silver or silver alloy.

Figure 9:
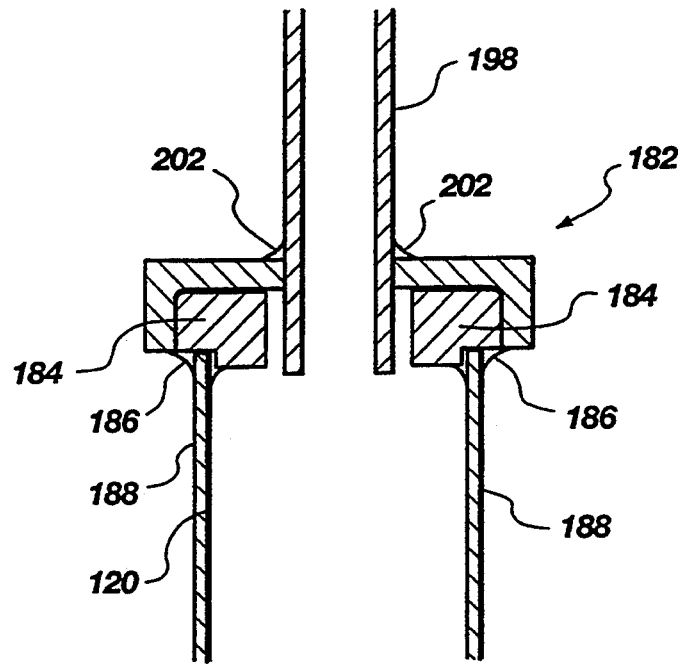
FIG. 9 is an enlarged view of a negative end cap illustrated in FIG. 7.
Figure 10:
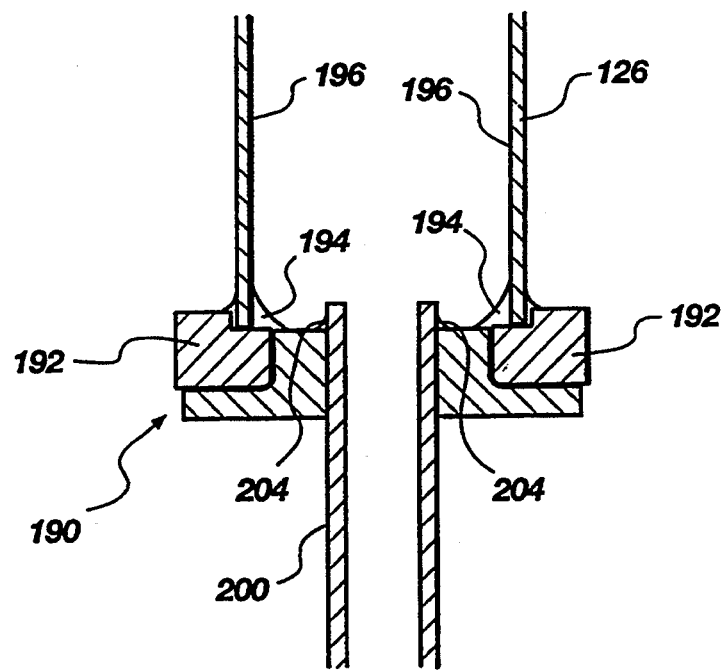
FIG. 10 is an enlarged view of a positive end cap illustrated in FIG. 7.

Referring to FIGS. 7, 9 and 10, a plurality of series tubular cells 120, 122, 124, 126 can be formed together by means of end caps 180 connected to the terminal cells 120, 126 of a series. A negative end cap 182 as shown in FIG. 9 is sealed to a ceria collar 184 of a first terminal cell 120 by sealant means as described previously. Conductive material 186 is positioned between the end cap 180, collar 184 and the cathode 188 of the cell 120. A positive end cap 190 as shown in FIG. 10 is sealed to the collar 192 of a second terminal cell 126 by sealing means previously described. Conductive material 194 is positioned between the end cap 190, the collar 192 and the anode 196 of the cell 126 to effect a pathway for electrons therebetween.

The material used for the end caps 180 of this embodiment is the same as described above in connection with the embodiment shown in FIGS. 1–6. Similarly, hollow conduits 198, 200 extend from the end caps 180 to provide communication of electrons and gases between integrated series of electrolytic cells. The end cap 190 is joined to the hollow conduit 198, 200 by either welding 202, 204, press fitting or the like.

The electrochemical device of the present invention provides an interconnected series of tubular electrolytic cells which maintains electrical and pneumatic integrity during operation. The configuration of the interconnect and the placement of sealant provides a gas-tight barrier between the internal and external environments of the electrolytic cells while avoiding deterioration or corrosion of the seal due to high operating temperatures. The electrochemical device of the present invention is adaptable to many applications, including oxygen generation. Thus, reference herein to specific details of the illustrated embodiments is by way of example and not by way of limitation. It will be apparent to those skilled in the art that many modifications of the basic illustrated embodiment may be made without departing from the spirit and scope of the ivention as recited by the claims.

What is claimed is:

1. An electrochemical solid-state device for transporting ions through a ceramic electrolyte comprising: a plurality of individual electrolytic cells, each said cell having an ion conducting electrolyte having a first surface and a second surface, an anode formed to said first surface, a cathode formed to said second surface and opposing ends, wherein each said electrolytic cell has the anode formed on the same surface;

conductive interconnecting structure positioned between an end of one electrolytic cell and an end of an adjacent electrolytic cell providing a pathway for movement of electrons between the anode of said one electrolytic cell and the cathode of said adjacent electrolytic cell; and sealing means for sealing said electrolytic cells to said interconnecting structure to provide a gas-tight seal therebetween, said sealing means being positioned relative to said conductive interconnecting structure to be spaced from said pathway for movement of electrons.

2. The electrochemical device according to claim 1 wherein each said electrolytic cell is cylindrically shaped having a central bore, and wherein said electrolytic cells are axially aligned and connected electrically in series.

3. The electrochemical device according to claim 2 wherein said ion conducting electrolyte of said electrolytic cells are formed of a ceramic metal oxide suitable for transporting oxygen ions therethrough.

4. The electrochemical device according to claim 3 wherein said ceramic metal oxide is selected from the group consisting of zirconia, ceria, hafnia and bismuth oxide.

5. The electrochemical device according to claim 4 wherein said ceramic metal oxides are doped.

6. The electrochemical device according to claim 3 wherein said anode and said cathode contain silver.

7. The electrochemical device according to claim 3 wherein said anode and said cathode contain a silver alloy containing at least fifty-percent silver.

8. The electrochemical device according to claim 3 wherein said conductive interconnecting structure is made of an oxidation-resistant metal.

9. The electrochemical device according to claim 3 wherein said conductive interconnecting structure is made of a semiconducting ceramic oxide.

10. The electrochemical device according to claim 9 wherein said semiconducting oxide is selected for the group consisting of lanthanum strontium manganite, lanthanum strontium chromite and lanthanum calcium manganite.

11. The electrochemical device according to claim 8 wherein said oxidation-resistant material is a stainless steel 446.

12. The electrochemical device according to claim 8 wherein said sealing means maintains a gas-tight seal at temperatures greater than 800° C. and has a thermal expansion rate comparable to that of the semiconducting material of the conductive interconnecting structure and said electrolyte.

13. The electrochemical device according to claim 12 wherein said sealing means is a devitrified glass.

14. The electrochemical device according to claim 9 wherein said sealing means maintains a gas-tight seal at temperatures greater than 800° C. and has a thermal expansion rate comparable to that of the semiconducting material of the conductive interconnecting structure and said electrolyte.

15. The electrochemical device according to claim 14 wherein said sealing means is a devitrified glass.

16. The electrochemical device according to claim 1 further including a positive end cap and a negative end cap, said positive end cap forming an electrical connection with the anode of a terminal electrolytic cell, said negative end cap forming an electrical connection with the cathode of another terminal electrolytic cell, said positive end cap being connectable to a negative end cap by conductive coupling structure providing electrical communication therebetween and providing pneumatic integrity to the device.

17. The electrochemical device according to claim 1 further including an annular collar surrounding said ends of each said electrolytic cell, each said annular collar being connected to said electrolytic cell to form a gas-tight seal therebetween, and said annular collar further being connected to said conductive interconnecting structure to form a gas-tight seal therebetween.

18. The electrochemical device according to claim 17 wherein said annular collar is formed from a material having a thermal expansion rate comparable to that of the electrolyte.

19. An electron conductor for joining together tubular electrolytic cells which have an ion-conducting electrolyte with internal and external opposing surfaces, an anode formed to one surface, a cathode formed to the opposing surface and two open ends, said electron conductor being bell-shaped and having a first end portion configured to be receivable within an open end of a tubular electrolytic cell and having a non-opposing second end portion configured to encircle an open end of an adjacent tubular electrolytic cell to provide electrical interconnection between the anode of one said electrolytic cell and the cathode of said adjacent electrolytic cell.

20. An electron conductor for joining together tubular electrolytic cells which have an ion-conducting electrolyte with internal and external opposing surfaces, an anode formed to one surface, a cathode formed to the opposing surface and two open ends, said electron conductor having a first end portion configured to be receivable within an open end of a tubular electrolytic cell and having a single radial surface positionable against the internal surface of said electrolytic cell, said electron conductor further having a non-opposing second end portion configured to encircle an open end of an adjacent tubular electrolytic cell and having a single radial surface positionable against the external surface of said cell to provide electrical interconnection between the anode of one said electrolytic cell and the cathode of said adjacent electrolytic cell.

21. The electron conductor according to claim 20 wherein said conductor is bell-shaped.

22. An electrochemical, solid-state device for transporting oxygen ions through a tubular ceramic electrolyte comprising:

a plurality of individual tubular electrolytic cells, each of said cells having a tubular, oxygen ion-conducting ceramic electroylyte with opposing surfaces, an anode coating on one surface of said tubular electroylte, a cathode coating on another surface of said tubular electrolyte and opposing open ends, wherein said tubular electrolytic cells are aligned and positioned with one open end of one tubular electrolytic cell juxtaposed in relation to an open end of an adjacent tubular electrolytic cell and each cell has the anode on the same surface, an electron conductor positioned between adjacent tubular electrolytic cells and configured to electrically connect the anode of one tubular cell to the cathode of an adjacent tubular cell; and sealing means to seal said electron conductor to each tubular electrolytic cell between which said electron conductor is positioned to prevent an interchange of gas from the exterior to the interior of said tubular electrolytic cells, said sealing means being electrolytic cell and said electron conductor.

23. The electrochemical device according to claim 22 wherein each said tubular electrolytic cell has a central bore, and further wherein said tubular electrolytic cells are axially aligned and positioned next to adjacent electrolytic cells in an end-to-end configuration.

24. The electrochemical device according to claim 23 wherein said anode is formed on the interior surface of said electrolyte of each said tubular electrolytic cell.

25. The electrochemical device according to claim 22 wherein said electrolyte is selected from the group consisting of zirconia, ceria, hafnia and bismuth oxide.

26. The electrochemical device according to claim 25 wherein said electrolyte material is doped.

27. The electrochemical device according to claim 24 wherein said anode and said cathode are silver.

28. The electrochemical device according to claim 24 wherein said anode and said cathode are made from a silver alloy containing at least fifty percent silver.

29. The electrochemical device according to claim 22 wherein said sealing means is a devitrified glass.

* * * * *

UNITED STATES PATENT AND TRADEMARK OFFICE
CERTIFICATE OF CORRECTION

PATENT NO. : 5,338,623
DATED : 8/16/94
INVENTOR(S) : Nachlas, et al.

It is certified that error appears in the above-indentified patent and that said Letters Patent is hereby corrected as shown below:

In Column 12, line 25, change "an" to --any--; and

In Column 12, line 28, after "being" insert --positioned between said tubular--.

Signed and Sealed this

Twenty-second Day of November, 1994

Attest:

BRUCE LEHMAN

Attesting Officer

Commissioner of Patents and Trademarks